United States Patent [19]

Vale, Jr. et al.

[11] E Re. 30,548

[45] Reissued Mar. 17, 1981

[54] PEPTIDES WHICH EFFECT RELEASE OF HORMONES

[75] Inventors: Wylie W. Vale, Jr.; Jean E. F. Rivier, both of La Jolla; Marvin R. Brown, Del Mar, all of Calif.

[73] Assignee: The Salk Institute for Biological Studies, San Diego, Calif.

[21] Appl. No.: 71,559

[22] Filed: Aug. 31, 1979

Related U.S. Patent Documents

Reissue of:

[64] Patent No.: 4,105,603
Issued: Aug. 8, 1978
Appl. No.: 781,580
Filed: Mar. 28, 1977

[51] Int. Cl.[3] ..... C08L 37/00; A61K 37/00; C07C 103/52

[52] U.S. Cl. ..... 260/8; 424/177; 260/112.5 S

[58] Field of Search ..... 260/112.5 S, 8; 424/177

[56] References Cited

U.S. PATENT DOCUMENTS

| | | | |
|---|---|---|---|
| 3,842,067 | 10/1974 | Sarantakis | 260/112.5 S |
| 3,882,098 | 5/1975 | Sarantakis | 260/112.5 S |
| 3,904,594 | 9/1975 | Guillemin et al. | 260/112.5 S |
| 3,917,578 | 11/1975 | Inmer et al. | 260/112.5 S |
| 3,933,784 | 1/1976 | Sarantakis | 260/112.5 S |
| 4,011,207 | 3/1977 | Sarantakis | 260/112.5 S |
| 4,105,603 | 8/1978 | Vale, Jr. et al. | 424/177 |

OTHER PUBLICATIONS

Burgus et al., Proc. Nat. Acad. Sci., 70, No. 3,pp. 684–688 (1973).

Brazeau et al., Science 179, pp. 77–79 (1973).

*Primary Examiner*—Delbert R. Phillips

*Attorney, Agent, or Firm*—Fitch, Even, Tabin, Flannery & Welsh

[57] ABSTRACT

The present invention relates to peptides which possess biological activity in respect to the inhibition of growth hormone, insulin [secretion] and glucagon secretion [are provided]. The peptides have fewer amino acid components than somatostatin and some of the peptides have dissociated activity.

7 Claims, No Drawings

PEPTIDES WHICH EFFECT RELEASE OF HORMONES

Matter enclosed in heavy brackets [ ] appears in the original patent but forms no part of this reissue specification; matter printed in italics indicates the additions made by reissue.

*The invention described herein was made in the course of work under a grant or award from the Department of Health and Human Services (formerly DHEW).*

The present invention relates generally to peptides having biological activity in respect to the inhibition of growth hormone, insulin and glucagon secretion. More particularly, the present invention is directed to peptides having fewer amino acid moieties than somatostatin which are effective to inhibit the release of growth hormone by the pituitary gland or the release of glucagon or insulin by the pancreas. Various peptides of the invention have dissociated biological activity in respect to the inhibition of growth hormone, insulin and glucagon secretion.

A peptide having inhibitory effect on the secretion of growth hormone has been characterized and is described in U.S. Pat. No. 3,904,594 to Guillemin et al. This peptide has been named "somatostatin". Somatostatin (also known as somatotropin release inhibiting factor) is the tetradecapeptide:

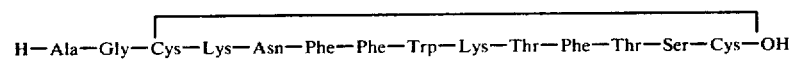

Somatostatin, the linear form of somatostatin (dihydrosomatostatin) and various acylated derivatives of somatostatin and dihydrosomatostatin are described in the aforementioned U.S. patent.

Somatostatin and many analogs of somatostatin exhibit activity in respect to the inhibition of growth hormone (GH) secretion from cultured, dispersed, rat anterior pituitary cells in vitro and inhibition of insulin and glucagon secretion in vivo in the rat. It has been considered highly desirable in the use of somatostatin to selectively inhibit only the secretion of GH, insulin or glucagon. Efforts have been made to develop analogs of somatostatin which possess dissociated biological activity and which inhibit only GH, insulin or glucagon secretion. Although there have been reports citing differences in the amounts of somatostatin required for inhibition of insulin compared to glucagon in the human and the perfused rat pancreas in vitro, somatostatin and some somatostatin analogs exhibit similar potencies on the inhibition of these two hormones in vivo.

The present invention relates to the discovery that certain amino acids can be removed and/or rearranged in somatostatin and dihydrosomatostatin peptides to provide novel peptides having fewer amino acid components and which possess biological activity in respect to the inhibition of GH, insulin or glucagon secretion. Some of the novel peptides of the invention have dissociated activity. The novel peptides of the invention having fewer amino acid components than somatostatin or dihydrosomatostatin are considered to be of great value because of the relative simplicity with which these peptides can be manufactured.

The novel peptides of the invention are defined by the formulae:

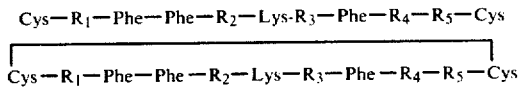

where $R_1$ is selected from Asn and des $R_1$, $R_2$ is selected from Trp and D-Trp, $R_3$ is selected from Phe and Thr, $R_4$ is selected from Thr and des $R_4$, and $R_5$ is selected from Ser, Phe, and des $R_3$ provided that at least one of $R_1$, $R_4$ and $R_5$ is deleted.

The nomenclature used to describe the peptides of the present invention is in accordance with the conventional practice of using the first three letters of the trivial name. Also, in accordance with such practice, it is the L form of the amino acid that is intended, unless otherwise expressly indicated. In this connection, it should be understood that either of the Cys amino acid moieties can be either D-Cys or L-Cys.

Pharmaceutically acceptable acid addition salts of the peptides are also within the scope of the present invention. Such acid addition salts include but are not limited to hydrochloride, hydrobromide, sulfate, phosphate, maleate, acetate, citrate, benzoate, succinate, malate, ascorbate, tartrate and the like.

Also considered to be within the scope of the present invention are intermediates of the formula:

wherein: X is either hydrogen or an α-amino protecting group. The α-amino protecting groups contemplated by X are those known to be useful in the art in the step-wise synthesis of polypeptides. Among the classes of α-amino protecting groups covered by X are (1) acyl type protecting groups such as formyl, trifluoroacetyl, phthalyl, toluenesulfonyl (tosyl), benzensulfonyl, nitrophenylsulfenyl, tritylsulfenyl, o-nitrophenoxyacetyl, chloroacetyl, acetyl, y-chlorobutyrul, etc.; (2) aromatic urethan type protecting groups such as benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups such as α-t-butyloxycarbonyl, diisopropylmethoxycarbonyl, isopropyloxycarbonyl, ethoxycarbonyl, allyloxycarbonyl; (4) cycloalkyl urethan type protecting groups such as cyclopentyloxycarbonyl, adamantyloxycarbonyl, cyclohexyloxycarbonyl; (5) thiourethan type protecting groups such as phenylthiocarbonyl; (6) alkyl type protecting groups such as triphenylmethyl (trityl), benzyl; (7) trialkylsilane groups such as trimethylsilane. The preferred α-amino protecting group defined by R is tertbutyloxycarbonyl.

$X^1$ and $X^6$ are each a protecting group for Cys selected from the group consisting of S-p-methoxybenzyl, S-p-methylbenzyl, S-acetamidomethyl, S-trityl, S-benzyl, and the like. The preferred protecting group is S-p-methoxybenzyl. $X^1$ and/or [$X^{5'}$] $X^6$ can be hydrogen which means that there is no protecting group on the sulfur group.

$X^2$ is a protecting group for the side chain amino substituent of lysine or $X^2$ is hydrogen which means there is no protecting group on the side chain amino substituent. Illustrative of suitable side chain amino protecting groups are benzyl, chlorobenzyloxycarbonyl, benzyloxycarbonyl, tosyl, t-amyloxycarbonyl, t-butyloxycarbonyl, etc. The selection of such a side chain amino protecting group is not critical except that it must be one which is not removed during deprotection of the α-amino groups during the synthesis. Hence, the α-amino protecting and side chain amino protecting group cannot be the same.

$X^3$, $X^4$ and $X^5$ are protecting groups for the hydroxyl group of Thr and Ser and are selected from the group consisting of acetyl, benzoyl, tert-butyl, trityl, tetrahydropyranyl, benzyl, 2,6-dichlorobenzyl and benzyloxycarbonyl. The preferred protecting group is benzyl. $X^3$ and/or $X^4$ and/or $X^5$ can be hydrogen which means there is no protecting group on the hydroxyl group.

$R_1$, $R_2$, $R_3$, $R_4$ and $R_5$ are as previously defined. $R_6$ is selected from the class consisting of OH, $OCH_3$, esters, amides, hydrazides and benzyl ester or hydroxymethyl ester anchoring bond used in solid phase synthesis linked to a solid resin support represented by the formulae:

—O—$CH_2$-polystyrene resin support and

O—$CH_2$-benzyl-polystyrene resin support

The polymer is preferably a copolymer of styrene with about 0.5 to 2.0% divinyl benzene as a cross-linking agent which causes the polystyrene polymer to be completely insoluble in certain organic solvents. In formula III at least one of X, $X^1$, $X^2$, $X^3$, $X^4$, $X^5$ and $X^6$ is a protecting group.

In selecting a particular side chain protecting group to be used in synthesis of the peptides of formula I or formula II, the following rules should be followed: (a) the protecting group must be stable to the reagent and under the reaction conditions selected for removing the α-amino protecting group at each step of the synthesis, (b) the protecting group must retain its protecting properties and not be split off under coupling conditions, and (c) the side chain protecting group must be removable upon the completion of the synthesis containing the desired amino acid sequence under reaction conditions that will not alter the peptide chain.

The peptides of formula I and formula II can be prepared using solid phase synthesis. The synthesis is commenced from the C-terminal end of the peptide using an α-amino protected resin. Such a starting material can be prepared by attaching an α-amino and S-protected Cys to a chloromethylated resin or a hydroxymethyl resin. The preparation of the hydroxymethyl resin is described by Bodanszky et al., Chem. Ind. (London) 38, 1597–98 (1966). A chloromethylated resin is commercially available from Bio Rad Laboratories, Richmond, California and the preparation of such a resin is described by Stewart et al., "Solid Phase Peptide Synthesis" (Freeman & Co., San Francisco 1969), Chapter 1, pp. 1–6. The α-amino and S-protected Cys is coupled to the chloromethylated resin according to the procedure of Monahan and Gilon, Biopolymer 12, pp. 2513–19, 1973. Following the coupling of the α-amino and S-protected Cys to the resin support, the α-amino protecting group is removed such as by using trifluoroacetic acid in methylene chloride, trifluoroacetic acid alone or HCl in dioxane. The deprotection is carried out at a temperature between about 0° C. and room temperature.

Other standard cleaving reagents and conditions for removal of specific α-amino protecting groups may be used as described in Schroder & Lubke, "The Peptides", 1 pp. 72–75 (Academic Press 1965).

After removal of the α-amino protecting group of Cys the remaining α-amino and side chain protected amino acids are coupled step-wise in the desired order to obtain a compound of formula III or as an alternate to adding each amino acid separately to the synthesis, some of them may be coupled prior to addition to the solid phase reactor. The selection of an appropriate coupling reagent is within the skill of the art. Particularly suitable as a coupling reagent is N,$N^1$-dicyclohexyl carbodiimide.

The activating reagents used in the solid phase synthesis of the peptides are those well known in the peptide art. Examples of suitable activating reagents are: (1) carbodiimides such as N,N-diisopropyl carbodiimide, N-ethyl $N^1$-(y-dimethylamino propyl carbodiimide); (2) cyanamides such as N,N-dibenzylcyanamide; (3) keteimines; (4) isoxazolium salts such as N-ethyl-5-phenyl isoxazolium-$3^1$-sulfonate; (5) monocyclic nitrogen containing heterocyclic amides of aromatic character containing one through 4 nitrogens in the ring such as imidazolides, pyrazolides, 1,2,4-triazolides. Specific heterocyclic amides that are useful include N,$N^1$-carbonyl diimidazole, N,$N^1$-carbonyl-di-1,2,4-triazole; (6) alkoxylated acetylene such as ethoxyacetylene; (7) reagents which form a mixed anhydride with the carboxyl moiety of the amino acid such as ethylchloroformate and isobutylchloroformate and (8) nitrogen-containing heterocyclic compounds having a hydroxy group on one ring nitrogen such as N-hydroxyphthalimide, N-hydroxysuccinimide and 1-hydroxybenzotriazole. Other activating reagents and their use in peptide coupling are described by Schroder & Lubke supra, in Chapter III and by Kapoor, J. Pharm. Sci., 59, pp. 1–27 (1970).

Each protected amino acid or amino acid sequence is introduced into the solid phase reactor in about a fourfold excess and the coupling is carried out in a medium of dimethylformamide: methylene chloride (1:1) or in dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid. The success of the coupling reaction at each stage of the synthesis is monitored by the ninhydrin reaction, as described by E. Kaiser et al., Analyt. Biochem. 34, 595 (1970).

After the desired amino acid sequence of formula III has been synthesized, the peptide is removed from the resin support by treatment with a reagent such as liquid hydrogen fluoride which not only cleaves the peptide from the resin but also cleaves all remaining side chain protecting groups $X^1$, $X^2$, $X^3$, $X^4$, $X^5$ and $X^6$ and the α-amino protecting group X to obtain directly a peptide of formula I. Peptides in accordance with formula II are obtained by oxidizing formula I peptides in accordance with known procedures. As an alternate route, the peptide linked to the resin support may be separated from the resin by alcoholysis after which the recovered C-terminal methyl ester is converted to the acid by hydrolysis. Any side chain protecting group may then be cleaved as previously described or by other procedures such as catalytic reduction (e.g. Pd on $BaSO_4$) using conditions which will keep the Trp moiety intact. When using hydrogen fluoride for cleaving, anisole is included in the reaction vessel as a scavenger.

The solid phase synthesis procedure discussed above is well known in the art and has been essentially described by Merrifield J. Am. Chem. Soc., 85, p. 2149 (1964).

The peptides of the present invention having dissociated effects in respect to inhibition of release of growth hormone, insulin and glucagon are considered to be particularly important in connection with the treatment of diabetes. The traditional view of diabetes has been that it is a disease resulting from impaired insulin production alone. As clinical and research experience has become more extensive, it has become apparent that some factor in addition to impairment of insulin secretion is operative in diabetes. It is known that, while insulin is normally deficient in diabetes, glucagon is normally present in excess. It is now believed that the presence of glucagon is at least as important a factor in diabetes as the absence of insulin.

The fact that a deficiency in insulin is normally accompanied by an excess of glucagon has made it difficult to study the role of glucagon in diabetes. While it is easy to add extra quantities of a hormone such as insulin, it has proved very difficult to lower the concentration of glucagon. The discovery of somatostatin has facilitated research in respect to the role of glucagon in diabetes. Somatostatin inhibits the release of both insulin and glucagon. The role of somatostatin in diabetes research is detailed in an article appearing in Science, Vol. 188, pp. 920–923, May 30, 1975. However, there are several problems in respect to the use of somatostatin as a treatment in diabetes. Somatostatin inhibits the release of insulin in addition to glucagon. Thus, the need for a peptide having a dissociated effect on the inhibition of release of insulin and glucagon has been recognized in connection with diabetes treatment. The novel peptides of the present invention provide such dissociative effect. More particularly, certain of the peptides of the present invention are effective to inhibit secretion of glucagon while having less effect on the inhibition of secretion of insulin.

The peptides of the invention provide the benefits of somatostatin and known somatostatin analogs, but have fewer amino acid components, e.g. 8 to 10 amino acid moieties as compared to 12 to 14 amino acid moieties for most known somatostatin analogs. Accordingly, the peptides of the present invention have significant economic advantage due to the relative ease of manufacture of these peptides.

The following examples illustrate various features of the present invention, but are intended to in no way limit the scope of the invention which is defined in the appended claims.

EXAMPLE I

The peptides of the present invention were synthesized by solid phase techniques, generally in accordance with the procedure described in U.S. Pat. No. 3,904,595. The synthesis was conducted in a stepwise manner on chloromethylated resin. The resin was composed of fine beads (20–70 microns in diameter) of a synthetic resin prepared by copolymerization of styrene with one to two percent divinylbenzene. The benzene rings in the resin were chloromethylated in a Friedel-Crafts reaction with chloromethyl methyl ether and stannic chloride. The chlorine thus introduced is a reactive benzyl chloride type of linkage. The Friedel-Crafts reaction is continued until the resin contains 0.5 to 2 millimoles of chlorine per gram of resin. In the further description of the synthesis of the peptides, the reagents used will be first described by their chemical name with their common abbreviation in parenthesis. Thereafter, the reagent will be referred to by the common abbreviation.

A peptide having the structure:

[H-Cys-Phe-Phe-D-Trp-Lys-Phe-Phe-Cys-OH]

*H-Cys-Phe-Phe-Trp-Lys-Thr-Phe-Cys-OH* was synthesized by the following solid phase methodology. Other peptides, described hereinafter were synthesized by a similar technique.

The tertiobutyloxycarbonyl-S-paramethoxybenzyl (Boc-SpOMe-Bzl) derivative of Cys was linked to the resin by any of three known methods; (1) reflux in ethanol in presence of triethyl amine, (2) Cesium salt of the Boc protected amino acid is kept at 50° C. in dimethylformamide (DMF) overnight, (3) the potassium salt of the Boc-protected amino acid is kept at 80° C. in dimethyl sulfoxide (DMSO) for 2 hours. Only one milliequivalent of the protected Cys per milliequivalent of Cl on the resin is used.

Method (3) is described hereinbelow in more detail. To a slurry of the resin and the dissolved protected Cys in DMSO is added 0.9 mEq of potassium tertiobutoxide (KOtBut) per mEq of amino acid. The reaction mixture is exposed to air as little as possible so that no amber coloration is observed. Reaction at 80° C. for 2 hours yields a suitable substituted resin for synthesis of the peptides (approx. 0.2 mEq of amino acid derivative per g of resin). After deprotection and neutralization, the peptide chain is built on resin. Deprotection, neutralization and addition of each amino acid is performed in accordance with schedule I. $N^{\alpha}$-t-butyloxycarbonyl (Boc) derivative of each amino acid is used. After deprotection of the first residue (i.e., SpOMe.Bzl.Cys) according to schedule I (steps 3 to 8 included), the N *Boc derivative of Phe is added along with a coupling agent. Thereafter, the N* Boc derivative of Thr is next added along with a coupling agent which is dicyclohexylcarbodiimide (DCC) (step 9 of schedule I). The side chain of Thr is protected with O-benzyl ether (OBzl). Benzyloxycarbonyl (Z) or benzyloxycarbonyl-2Cl [Z(2-Cl)] was used as the protecting group for the Lys side chain.

1. Schedule for coupling of amino acids in solid phase synthesis (5–10 g resin)

| Step | Reagents and operations | Mix times Min. |
|---|---|---|
| 1 | $CH_2Cl_2$ wash 80 ml (2 times) | 3 |
| 2 | Methanol (MeOH) wash 30 Ml (2 times) | 3 |
| 3 | $CH_2Cl_2$ wash 80 ml (3 times) | 3 |
| 4 | 50 percent trifluoroactetic acid (TFA) containing 5 percent 1,2-ethanedithiol in $CH_2Cl_2$ 70 ml (2 times) | 10 |
| 5 | $CH_2Cl_2$ wash 80 ml (2 times) | 3 |
| 6 | Triethylamine ($Et_2N$) 12.5 percent in $CH_2Cl_2$ 70 ml (2 times) | 5 |
| 7 | MeOH wash 40 ml (2 times) | 2 |
| 8 | $CH_2Cl_2$ wash 80 ml (3 times) | 3 |
| 9 | Boc-amino acid (10 mmoles) in 10 ml DMF (1 times) and 30 ml $CH_2Cl_2$ plus DCC (10 mmoles) in | |

-continued

| I. Schedule for coupling of amino acids in solid phase synthesis (5-10 g resin) | | |
|---|---|---|
| Step | Reagents and operations | Mix times Min. |
| | $CH_2Cl_2$ (2 M) | 30 to 120 |
| 10 | MeOH wash 40 ml (2 times) | 3 |
| 11 | $Et_3N$ 12.5 percent in $CH_2Cl_2$ 70 ml (2 times) | 3 |
| 12 | MeOH wash 30 ml (2 times) | 3 |
| 13 | $CH_2Cl_2$ wash 80 ml (2 times) | 3 |

After step 13, an aliquot is taken for a ninhydrin test: if the test is negative, go back to step 1 for coupling of the next amino acid; if the test is positive or slightly positive, go back to steps 9 through 13. Schedule I was used for coupling of each of the amino acids of the peptide to Cys.

Cleavage of the peptides from the resin (5 grams) and deprotection of the side chain protecting groups of the peptide was performed in hydrofluoric acid (75 ml) in the presence of anisole (8 ml). After elimination of hydrofluoric acid under high vacuum, the resin-peptide was washed with ether.

The dried resin was immediately extracted with 25% acetic acid (150 ml) and diluted to 3000 ml with degassed $H_2O$ ($N_2$). The pH of the solution was adjusted to 6.6–7.0 with $NH_4OH$. The solution was titrated dropwise under stirring with potassium ferricyanide solution (1.g/500 ml $H_2O$) until a permanent yellow color was observed. The solution sat for 10 minutes and pH was adjusted to 5.0 with glacial acetic acid; Bio Rad AG 3-X4A resin (100–200 mesh, chloride form, 10–15 g) was added to the turbid solution and stirred for 15 minutes. The solution was filtered over celite and applied successively onto two columns; (a) Bio Rad AG 3-X4A resin chloride form (10 ml); (b) Bio Rex-70 resin (100 ml) cation form. The celite + resin cake was thoroughly washed with water (500 ml) which was applied onto columns (a) and (b) as a wash. The peptide material was then eluted from the Bio Rex-70 resin column with pyridine; acetic acid:water (30:4:66) or 50% acetic acid. Fractions were collected; only the ones containing peptide (ninhydrin positive) were diluted with water and immediately lyophilized. 950 mg of crude cream colored material was obtained. It was applied onto a Sephadex G-25 F gel column (3×200 cm) equilibrated and eluted with 2 N acetic acid.

The elution pattern as observed at 280 nm showed one major symmetrical peak. After lyophylization the center cut yielded 550 mg which were submitted to counter current distribution (solvent system n-butanol:acetic acid:water, 4:1:5) 10 ml lower phase per tube. 100 transfers were performed and the major peak was found in tubes 57–68. The compound (250 mg) appeared homogeneous on tlc.

The specific optical rotation was $[\alpha]^{23} = -67.8 \pm 2$: (c=1 in 1% acetic acid). Amino acid analysis of this material showed the expected ratio for the different amino acids.

Active esters can be used in solid phase synthesis and the classical method of synthesis can also be used to prepare the peptides of the invention.

In vitro Bioassay: The effects of the various peptides of the invention were tested in vitro on the secretion of growth hormone by primary cultures of enzymatically dissociated rat anterior pituitary cells by the method of Vale et al., Endocrinology 91: p. 562–571 (1972). The assay is made by treating pituitary glands removed from rats to separate cells therefrom. The cells are placed in culture dishes in Dulbecco's Modified Eagle Medium (Dulbecco et al., Virology, Vol. 8, p. 396, 1949). Carbon dioxide gas and oxygen are supplied to the cell cultures which are maintained at 37° C. for 4–5 days prior to use in the assay. Following media changes, cell cultures are incubated for a period of 4 hours and particular somatostatin peptides are added thereto. Radioimmunoassay analysis is used to determine the rate of growth hormone secretion which is expressed in nanograms per hour.

An investigation of the effect of somatostatin, dihydrosomatostatin, (as controls) and the peptides of the invention to inhibit the release of glucagon and insulin was made as follows:

In vivo Bioassay: Male Sprague-Dawley-CD rats weighing 180–200 g housed in temperature and humidity controlled quarters with 14h light and 10h dark (light 0700–21100) were used in all experiments. Animals were fed a standard ration and tap water ad libitum. Experiments were carried out at least 5 days after arrival of rats from the supplier between the hours 1400 to 1600. After ether anesthesia, peptides or saline were administered in a volume of 0.2 ml. via the external jugular vein. Animals remained anesthetized until the time of blood collection from the portal vein. The blood samples were placed into chilled tubes containing 10 mg EDTA and 50 μl of M Benzamidine per ml of blood.

Plasma was stored at −20° C. for insulin and glucagon determinations. Insulin levels were determined by the method of Herbert et al, J. Chem. Endocr. Metab. 25:1375, [1956] *1965*, utilizing porcine insulin antisera and (125I) iodinated insulin tracer. Human insulin standard was obtained from Schwarz-Mann, Orangeburg, New York. Glucagon was determined by the method of Faloona and Unger, in Jaffe et al ed., Methods of Hormone Radioimmunoassay, Academic Press, New York, 1974, p. 317, utilizing glucagon antisera 30K. Cellulose was determined by the glucose oxidase method, utilizing a Beckman Glucose Analyzer.

GH determinations were performed on tissue culture media utilizing the following reagents: NIAMDD rat GH standard (GH-RP-1), NIAMDD monkey anti-rat GH (GH-Serum-3), and highly purified rat GH for iodination.

All experiments were carried on in a randomized block design. Following analysis of variance difference between treatments were determined by the multiple range tests of Dunnett and Duncan. Potency values were calculated from four or six point bioassays.

Various peptides in accordance with the invention were prepared in accordance with the solid phase methodology described above. The composition of the peptides is reported hereinbelow in Table I. Table I also sets forth the percent effectiveness of the peptide for inhibiting secretion of growth hormone (GH), insulin and glucagon, with somatostatin taken as the base.

TABLE I

| | | Somatostatin (control) Peptides of Invention | | | Growth Hormone | Insulin | Glucagon |
|---|---|---|---|---|---|---|---|
| $R_1$ | $R_2$ | $R_3$ | $R_4$ | $R_5$ | 100 | 100 | 100 |
| des$R_1$ | D-Trp | [Phe] *Thr* | des$R_4$ | des$R_5$ | 6 | 80 | 100 |
| des$R_1$ | D-Trp | [Phe] *Thr* | des$R_4$ | des$R_5$(D-Cys)$^{11}$ | 14 | 100 | 100 |
| des$R_1$ | D-Trp | [Phe] *Thr* | Thr | des$R_5$ | 35 | 10-100 | 100 |
| Asn | D-Trp | [Phe] *Thr* | des$R_4$ | des$R_5$ | <1 | 100 | <1 |
| Asn | Trp | [Phe] *Thr* | Thr | des$R_5$ | 3 | 100 | <1 |
| Asn | D-Trp | [Phe] *Thr* | Thr | des$R_5$ | 10 | 200 | 10-100 |

What is claimed is:

1. A peptide selected from those of the formulae:

$$\text{Cys}-R_1-\text{Phe}-\text{Phe}-R_2-\text{Lys}-R_3-\text{Phe}-R_4-R_5-\text{Cys} \quad \text{I}$$

$$\text{Cys}-R_1-\text{Phe}-\text{Phe}-R_2-\text{Lys}-R_3-\text{Phe}-R_4-R_5-\text{Cys} \quad \text{II}$$

$$X-\text{Cys}-(X^1)-R_1-\text{Phe}-\text{Phe}-R_2-\text{Lys}(X^2)-R_3(X^3)-\text{Phe}-R_4(X^4)-R_5(X^5)-\text{Cys}(X^6)-R_6 \quad \text{III}$$

wherein $R_1$ is selected from the group consisting of Asn and des$R_1$; $R_2$ is selected from the group consisting of Trp and D-Trp; $R_3$ is selected from the group consisting of Phe and Thr; $R_4$ is selected from group consisting of Thr and des$R_4$; $R_5$ is selected from the group consisting of Ser, Phe and des$R_5$, provided that at least one of $R_1$, $R_4$ and $R_5$ is deleted; X is selected from the group consisting of H, and an alpha-amino protecting group; $X^1$ and $X^6$ are selected from the group consisting of H and a protecting group for Cys selected from S-p-methoxybenzyl, S-acetamidomethyl, S-trityl and S-benzyl; $X^2$ is selected from the group consisting of H and a side chain amino protecting group; $X^3$, $X^4$ and $X^5$ are selected from the group consisting of H and a hydroxyl protecting group selected from the group consisting of acetyl, benzoyl, tert-butyl, trityl, benzyl and benzyloxycarbonyl; with the proviso that at least one of X, $X^1$, $X^2$, $X^3$, $X^4$, $X^5$, and $X^6$ is other than hydrogen; [and] $R_6$ is selected from the group consisting of hydroxy, methoxy, and an anchoring bond used in solid phase synthesis linked to a solid resin support selected from the group consisting of —O—$CH_2$-polystyrene resin support and O—$CH_2$-benzylpolystyrene resin support; *and Cys is either L-Cys or D-Cys.*

2. A peptide in accordance with claim 1 wherein $R_1$ is des $R_1$, $R_2$ is D-Trp, $R_3$ is [Phe] *Thr*, $R_4$ is des$R_4$ and $R_5$ is des$R_5$.

3. A peptide in accordance with claim 1 wherein $R_1$ is des$R_1$, $R_2$ is D-Trp, $R_3$ is [Phe] *Thr*, $R_4$ is Des$R_4$, $R_5$ is des$R_5$ and [D-Cys is substituted for] Cys$^{11}$ *is D-Cys.*

4. A peptide in accordance with claim 1 wherein $R_1$ is des$R_1$, $R_2$ is D-Trp, $R_3$ is [Phe] *Thr*, $R_4$ is [des$R_4$] *Thr* and $R_5$ is des$R_5$.

5. A peptide in accordance with claim 1 wherein $R_1$ is Asn, $R_2$ is D-Trp, $R_3$ is [Phe] *Thr*, $R_4$ is des$R_4$ and $R_5$ is des$R_5$.

6. A peptide in accordance with claim 1 wherein $R_1$ is Asn, $R_2$ is Trp, $R_3$ is [Phe] *Thr*, $R_4$ is Thr and $R_5$ is des$R_5$.

7. A peptide in accordance with claim 1 wherein $R_1$ is Asn, $R_2$ is D-Trp, $R_3$ is [Phe] *Thr*, $R_4$ is Thr and $R_5$ is des $R_5$.

* * * * *